United States Patent
Wang et al.

(10) Patent No.: US 12,402,968 B2
(45) Date of Patent: Sep. 2, 2025

(54) MINIMALLY INVASIVE SURGICAL ROBOT MASTER MANIPULATOR AND SLAVE MANIPULATOR CONTROL METHOD

(71) Applicant: CHONGQING JINSHAN MEDICAL ROBOTICS CO., LTD., Chongqing (CN)

(72) Inventors: Liao Wang, Chongqing (CN); Jiang Hu, Chongqing (CN); Yu Huang, Chongqing (CN); Yong Wang, Chongqing (CN); Jinshan Wang, Chongqing (CN)

(73) Assignee: CHONGQING JINSHAN MEDICAL ROBOTICS CO., LTD., Chongqing (CN)

( * ) Notice: Subject to any disclaimer, the term of this patent is extended or adjusted under 35 U.S.C. 154(b) by 522 days.

(21) Appl. No.: 17/788,773

(22) PCT Filed: Sep. 14, 2020

(86) PCT No.: PCT/CN2020/114986
§ 371 (c)(1),
(2) Date: Jun. 24, 2022

(87) PCT Pub. No.: WO2021/139203
PCT Pub. Date: Jul. 15, 2021

(65) Prior Publication Data
US 2023/0033189 A1 Feb. 2, 2023

(30) Foreign Application Priority Data
Jan. 10, 2020 (CN) .......................... 202010025695.4

(51) Int. Cl.
*A61B 34/37* (2016.01)
*A61B 34/00* (2016.01)
(Continued)

(52) U.S. Cl.
CPC .............. *A61B 34/71* (2016.02); *A61B 34/20* (2016.02); *A61B 34/37* (2016.02);
(Continued)

(58) Field of Classification Search
CPC ......... B25J 3/00; B25J 3/04; B25J 3/02; B25J 9/06; B25J 9/046; A61B 2034/742
See application file for complete search history.

(56) References Cited

U.S. PATENT DOCUMENTS

| 6,684,129 | B2 * | 1/2004 | Salisbury, Jr. ......... | A61B 34/30 600/595 |
| 9,293,962 | B2 * | 3/2016 | Park ...................... | H02K 11/21 |
| 2012/0011956 | A1 | 1/2012 | Lundberg | |

FOREIGN PATENT DOCUMENTS

| CN | 101623864 A | 1/2010 |
| CN | 102395449 A | 3/2012 |

(Continued)

OTHER PUBLICATIONS

International Search Report for PCT/CN2020/114986 mailed Dec. 9, 2020, ISA/CN.
(Continued)

*Primary Examiner* — Gregory Robert Weber
(74) *Attorney, Agent, or Firm* — Yue (Robert) Xu; Apex Attorneys at Law, LLP

(57) ABSTRACT

A master manipulator includes a first master manipulator module, a second master manipulator module, and a third master manipulator module which are perpendicular to each other, an output end of the third master manipulator module is connected to an input end of the second master manipulator module; an output end of the second master manipulator module is connected to an input end of the first master manipulator module; the first master manipulator module can be connected to a main controller. The minimally invasive surgery robot master manipulator is simple and (Continued)

compact in structure, and can realize a high-precision surgical operation; moreover, the master manipulator modules are located above a transverse third master arm, thereby reducing the size of each master manipulator in a vertical direction, and effectively avoiding interference between the master manipulator and other components in the vertical direction.

21 Claims, 6 Drawing Sheets

(51) Int. Cl.
  *A61B 34/20*  (2016.01)
  *A61B 90/00*  (2016.01)
(52) U.S. Cl.
  CPC . *A61B 2034/2059* (2016.02); *A61B 2034/742* (2016.02); *A61B 34/76* (2016.02); *A61B 2090/066* (2016.02)

(56) References Cited

FOREIGN PATENT DOCUMENTS

| | | |
|---|---|---|
| CN | 106214257 A | 12/2016 |
| CN | 107374727 A | 11/2017 |
| CN | 208592849 U | 3/2019 |
| CN | 209734150 U | 12/2019 |
| CN | 211583482 U | 9/2020 |
| CN | 211862956 U | 11/2020 |
| CN | 211884027 U | 11/2020 |
| WO | 2017081137 A1 | 5/2017 |

OTHER PUBLICATIONS

Chinese first Office Action issued on Dec. 27, 2024 for the Chinese priority application No. 202010025695.4.

\* cited by examiner

MINIMALLY INVASIVE SURGICAL ROBOT MASTER MANIPULATOR AND SLAVE MANIPULATOR CONTROL METHOD

This application is a National Phase entry of PCT Application No. PCT/CN2020/114986, filed on Sep. 14, 2020, which claims the priority to Chinese patent application No. 202010025695.4, titled as "CONTROL METHOD FOR MASTER MANIPULATOR AND SLAVE MANIPULATOR OF MINIMALLY INVASIVE SURGICAL ROBOT", filed with the Chinese State Intellectual Property Office on Jan. 10, 2020, the entire disclosures of which are incorporated herein by reference.

FIELD

The present application relates to the technical field of medical robots, and in particular to a master manipulator of a minimally invasive surgical robot.

BACKGROUND

Minimally invasive surgery is widely used because of its small injury and fast healing. In the conventional technology, a minimally invasive surgical robot generally has a master controller arranged at a rear end of a master manipulator. When the master controller is manipulated, each axis of the master manipulator generates movement, and then a signal is sent to a control center. After the signal is processed, it is further sent to a slave manipulator to control an instrument to move and complete the surgery. Since all axes of the master manipulator generate movement when the control center processes the signal, the amount of data processed by the control center is large, which causes a long data processing time and a delay from the hand action to the surgery action.

In addition, the structure of the master manipulator in the conventional technology, such as a master manipulator disclosed by CN106667583A, has a complex structure and a large volume for realizing multiple degrees of freedom. A relatively precise machining is needed in order to achieve precise surgical operation, which directly increases the manufacturing cost.

Besides, the size of the surgical robot should be as small as possible, especially the size of the master manipulator in a vertical direction should be minimized, so as to avoid the interference between the master manipulator and other components in the vertical direction.

Therefore, those skilled in the art are dedicated to develop a master manipulator of a minimally invasive surgical robot with a simple and compact structure which can effectively avoid interference.

SUMMARY

In view of the above disadvantages of the conventional technology, the technical problem to be solved by the present application is to provide a master manipulator of a minimally invasive surgical robot with a simple and compact structure.

In order to achieve the above object, a master manipulator of a minimally invasive surgical robot is provided according to the present application, which includes a first master manipulator module, a second first master manipulator module and a third master manipulator module which are perpendicular to each other; an output end of the third master manipulator module is connected to an input end of the second master manipulator module; an output end of the second master manipulator module is connected to an input end of the first master manipulator module; and the first master manipulator module is connected to a master controller.

Preferably, the first master manipulator module and the second master manipulator module are connected by a first master arm; the second master manipulator module is provided with a second master arm; the third master manipulator module is provided with a third master arm which is transverse; and one end, away from the third master manipulator module, of the third master arm is connected to one end, away from the second master manipulator module, of the second master arm.

Preferably, a centerline of the first master manipulator module and a centerline of the second master manipulator module are located on a same plane.

Preferably, a rotatable driving member is provided at the end, away from the third master manipulator module, of the third master arm; a second connecting rod is provided at the end, away from the second master manipulator module, of the second master arm; and the second connecting rod is connected to a driving member in a power transmitted manner.

Preferably, the driving member is connected to the third master manipulator module through a belt transmission mechanism in a power transmitted manner.

In order to simplify the calculation of the control center, a center of the first master manipulator module, a center of the second master manipulator module and a center of the driving member meet at a same point.

Preferably, the third master arm includes a third connecting rod which is transverse; a third joint module is provided at one end of the third connecting rod; a third fixing seat which is fixedly connected to a fourth master manipulator module of the master manipulator is provided on a housing of the third joint module; and the driving member is arranged at the other end of the third connecting rod.

Preferably, the second master arm is L-shaped; the second master arm includes a second fixing seat; a second joint module is provided on the second fixing seat; one end of the second fixing seat is fixedly connected to a second cover plate A and the second connecting rod sequentially; the other end of the second fixing seat is fixedly connected to a second cover plate B; and the second cover plate B is fixedly connected to the second connecting rod.

Preferably, the first master arm is L-shaped; one end of the first master arm is fixedly connected to the first master manipulator module, and the other end of the first master arm is fixedly connected to the output end of the second master manipulator module.

Preferably, the first master manipulator module includes a first fixing seat; a first joint module is provided on the first fixing seat; one end of the first fixing seat is fixedly connected to a first cover plate A, a first cover plate B and a first connecting rod sequentially; the other end of the first fixing seat is fixedly connected to a first cover plate C and a first cover plate D sequentially; and the first cover plate D is fixedly connected to the first connecting rod.

Preferably, the master manipulator of the minimally invasive surgical robot further includes a fourth master manipulator module, a fifth master manipulator and a sixth master manipulator which are arranged vertically from bottom to top; and the fourth master manipulator module is fixedly connected to the third master manipulator module.

Preferably the fourth master manipulator module, the fifth master manipulator and the sixth master manipulator all include a joint module;

the joint module includes a base; a housing is fixedly connected to the base; a motor is provided on the housing through a rolling bearing and a rolling bearing; an output shaft of the motor is connected to a reducer through a connecting flange; the reducer is arranged on the base through a cross rolling bearing; and the reducer transmits power to an output flange.

In order to accurately control a position of the master arm, a position encoder is provided on an outer circular surface of the output flange.

Preferably, an output end of the reducer is fixed to a connecting flange; the output flange is fixedly connected to the connecting flange; and a torque sensor is provided between the connecting flange and the output flange.

Preferably, one end, away from the output flange, of the base is fixed to a cable sleeve fixing seat; a cable sleeve is fixed in the cable sleeve fixing seat; the cable sleeve is passed through the motor and the reducer sequentially; and the cable sleeve is supported on the connecting flange through a rolling bearing.

In order to measure a motion parameter of the motor, a speed encoder is provided at one end, away from the output flange, of the cable sleeve.

Preferably, a structure of the first master manipulator module and a structure of the third master manipulator module and a structure of the second master manipulator module are same, which all include a housing and a joint module which is arranged in the housing;

the joint module includes a base which is fixedly connected to the housing; a motor is provided on the base through a first bearing; an output shaft of the motor is connected to a reducer; the reducer is arranged on the base through a bearing; the reducer transmits power to an output flange;

one end of the first master arm is fixed to the housing of the first master manipulator module, the other end of the first master arm is fixed to an output flange of the second master manipulator module;

one end of the second master arm is fixed to the housing of the second master manipulator module, the other end of the second master arm is fixed to an output flange of the third master manipulator module; and one end of the third master arm is fixed to the output flange of the third master manipulator module.

Preferably, a position encoder is provided on an outer circular surface of the output flange.

Preferably, an output end of the reducer is fixed to an intermediate member; and the output flange is fixedly connected to the intermediate member.

Preferably, a torque sensor is provided between the intermediate member and the output flange.

Preferably, a cable sleeve fixing seat is provided at one end, away from the output flange, of the base; a cable sleeve is fixed in the cable sleeve fixing seat; the cable sleeve is passed through the motor and the reducer sequentially; and the cable sleeve is supported by spaced bearings.

Preferably, a speed encoder is provided at one end, away from the output flange, of the cable sleeve.

Preferably, the output flange of the second master manipulator module is fixed to a first disc-shaped member by a bolt; the first disc-shaped member is fixed to a second disc-shaped member by a bolt; and an edge of the second disc-shaped member is fixed to a rear end of the first master arm by a bolt; and the output flange of the third master manipulator module is fixed to a third disc-shaped member by a bolt; the third disc-shaped member is fixed to a fourth disc-shaped member by a bolt; and an edge of the fourth disc-shaped member is fixed to a rear end of the second master arm by a bolt.

Preferably, the first master manipulator module and the second master manipulator module are connected by a first master arm; the third master manipulator module and the second master manipulator module are connected by a second master arm; and the third master manipulator module is fixed to a fourth master manipulator module of the minimally invasive surgical robot by a third master arm.

Preferably, a centerline of the first master manipulator module and a centerline of the third master manipulator module are located on a same plane; or the centerline of the third master manipulator module and a centerline of the second master manipulator module are located on a same plane; or the centerline of the first master manipulator module and the centerline of the second master manipulator module are located on a same plane.

Preferably, a center of the first master manipulator module, a center of the third master manipulator module and a center of the second master manipulator module meet at a same point.

A method for controlling a slave manipulator of a minimally invasive surgical robot includes the following steps:

1), providing multiple master manipulator modules; in which the master manipulator module located upstream is rotatably connected to the master manipulator module located downstream;

2), connecting the master manipulator module at a head end or a tail end with a master controller; in which when the master controller moves, a moving direction or a decomposition direction of the moving direction according to a preset coordinate system of the master controller always passes through a centerline of one or more master manipulator module;

3), sending a signal of its own movement parameters by each master manipulator module to a control center when the master controller moves; in which the movement parameters include a movement speed, an angle and a displacement; and 4), receiving the signal of each master manipulator by the control center, obtaining movement parameters of the slave manipulator by calculation, and then controlling the slave manipulator to act according to the movement parameters of the slave manipulator; in which the movement parameters of the slave manipulator include a movement speed, an angle and a displacement.

Preferably, the master manipulator module connected to the master controller and the two master manipulator modules adjacently connected to the master manipulator module connected to the master controller are perpendicular to each other.

Preferably, a centerline of the master controller and centerlines of the two master manipulator modules adjacently connected to the master controller meet at one point.

Preferably, a centerline of the master manipulator module connected to the master controller and centerlines of the two master manipulator modules adjacently connected to the master manipulator which is connected to the master controller meet at one point.

The beneficial effects according to the present application are: the master manipulator of the minimally invasive surgical robot has a compact structure and can realize high precision surgical operation; in addition, the master manipulator modules are located above the third master arm which is transverse, which reduces the size of the master manipulator in the vertical direction and effectively avoids the interference between the master manipulator and other components in the vertical direction.

DETAILED DESCRIPTION OF THE EMBODIMENTS

Figure 1:
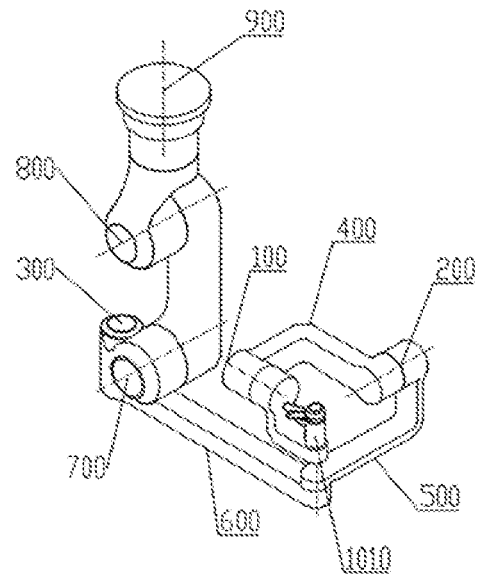
FIG. 1 is a schematic structural view of a master manipulator of a minimally invasive surgical robot according to a first embodiment of the present application.
Figure 2:
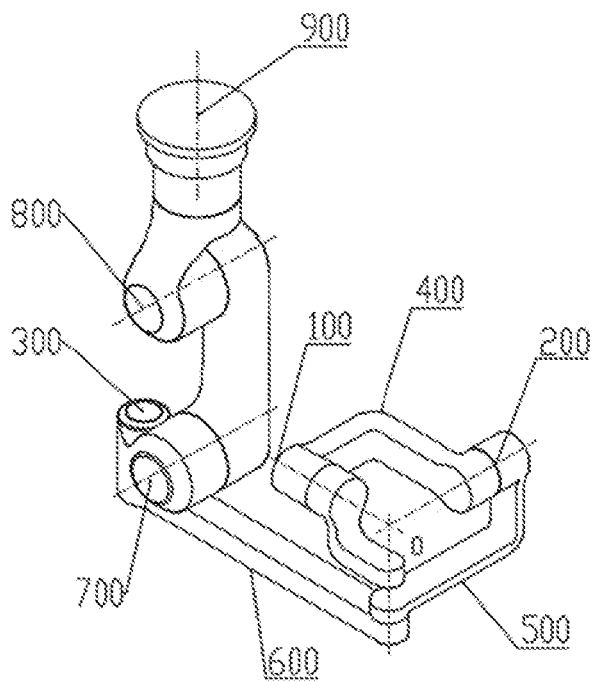
FIG. 2 is a schematic structural view of the master manipulator of the minimally invasive surgical robot according to the first embodiment of the present application.
Figure 3:
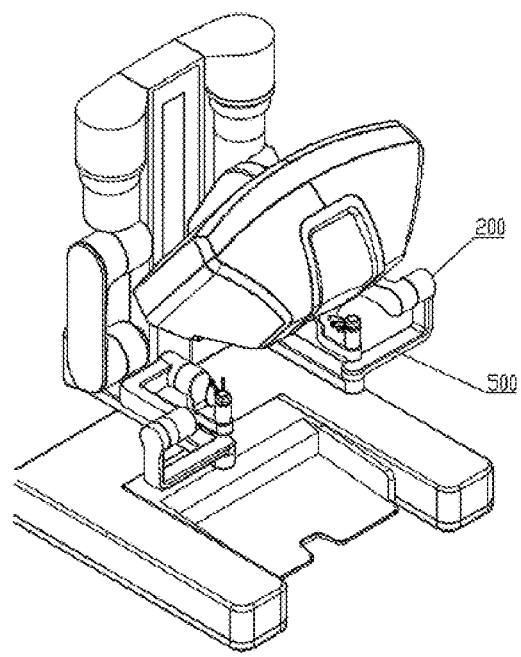
FIG. 3 is a schematic structural view of the master manipulator of the minimally invasive surgical robot mounted on the minimally invasive surgical robot according to the first embodiment of the present application.
Figure 4:
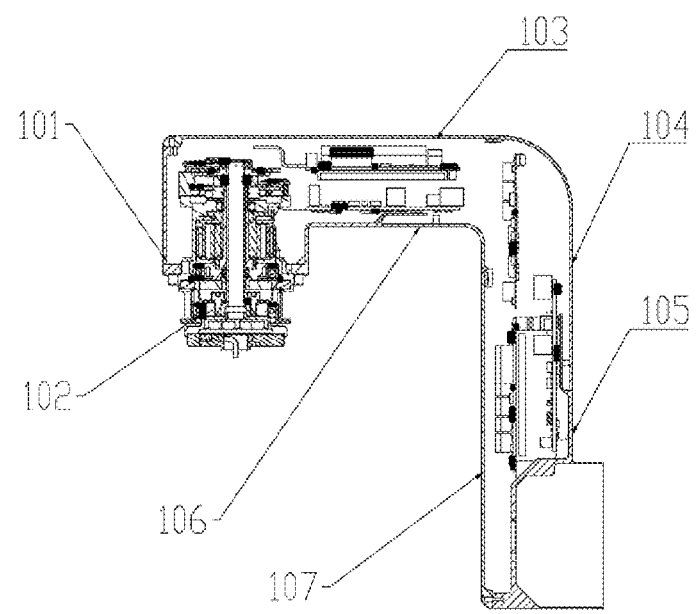
FIG. 4 is a schematic structural view of a first master manipulator module of the master manipulator of the minimally invasive surgical robot according to the first embodiment of the present application.
Figure 5:
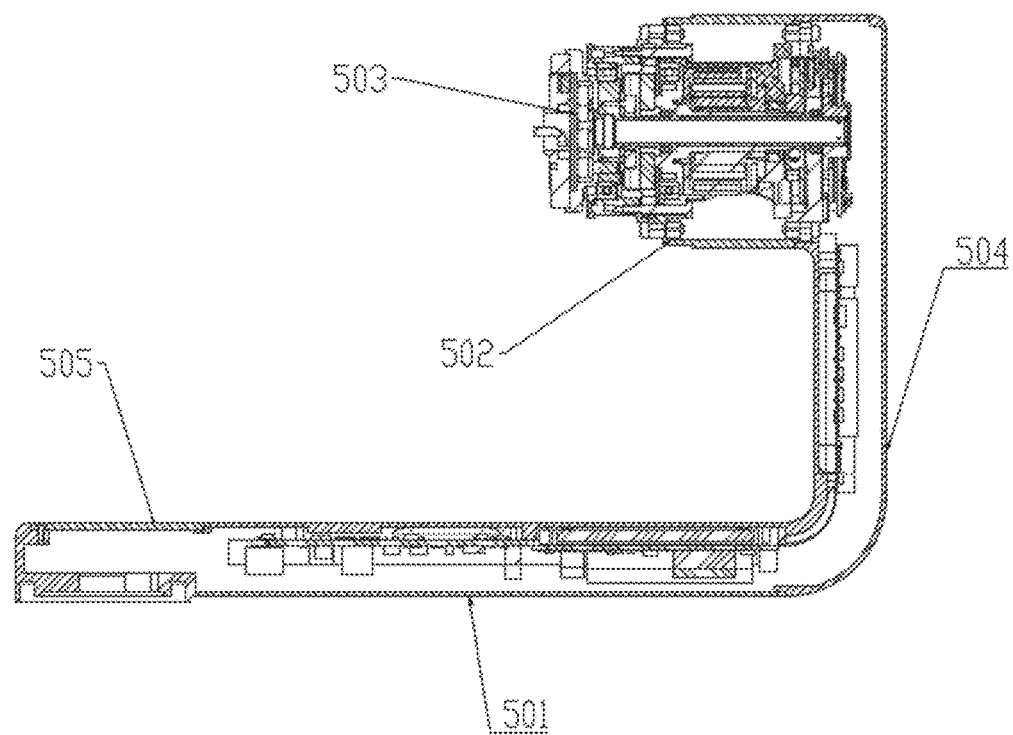
FIG. 5 is a schematic structural view of a second master arm of the master manipulator of the minimally invasive surgical robot according to the first embodiment of the present application.
Figure 6:
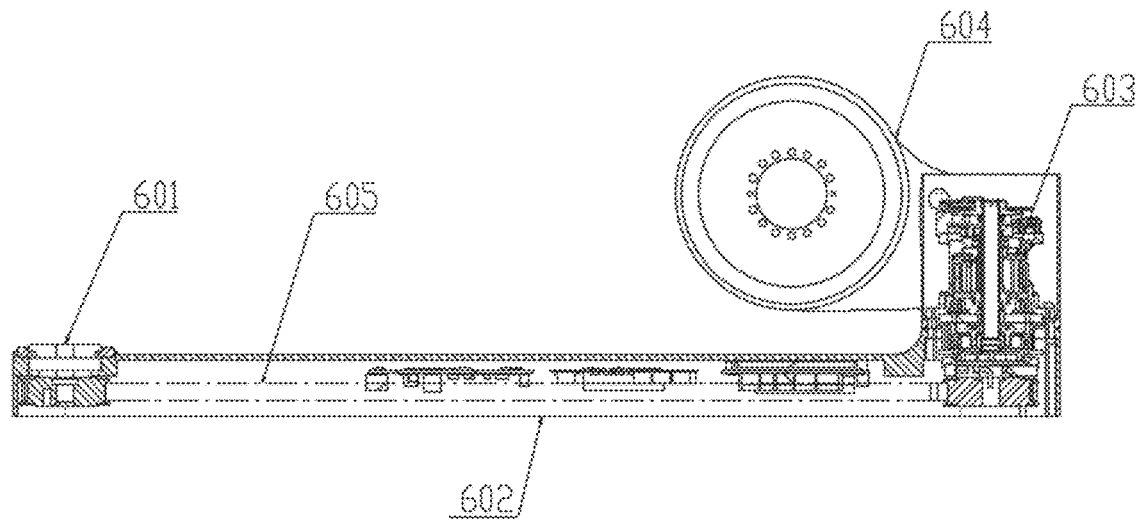
FIG. 6 is a schematic structural view of a third master arm of the master manipulator of the minimally invasive surgical robot according to the first embodiment of the present application.
Figure 7:
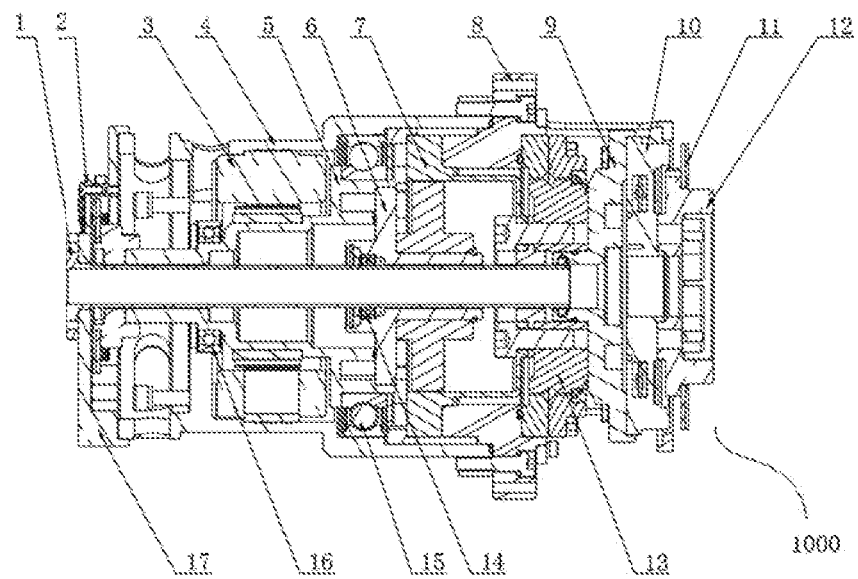
FIG. 7 is a schematic structural view of a joint module of the first master manipulator module of the master manipulator of the minimally invasive surgical robot according to the first embodiment of the present application.
Figure 8:
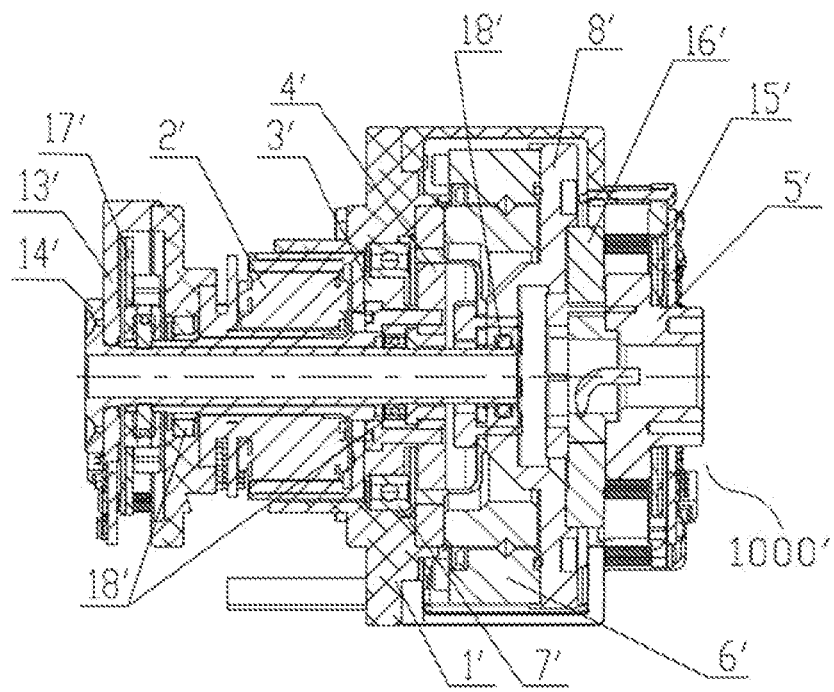
FIG. 8 is a schematic structural view of a joint module of a fourth master manipulator module of the master manipulator of the minimally invasive surgical robot according to the first embodiment of the present application.

The present application is further described in combination with the accompanying drawings and the embodiments.

A method for controlling a slave manipulator of a minimally invasive surgical robot includes the following steps:
1), providing multiple master manipulator modules; in which the master manipulator module located upstream is rotatably connected to the master manipulator module rotatably located downstream;
2), connecting the master manipulator module at a head end or a tail end with a master controller; in which when the master controller moves, a moving direction or a decomposition direction of the moving direction according to a preset coordinate system of the master controller always passes through a centerline of one or more master manipulator module;
3), sending a signal of its own movement parameters by each master manipulator module to a control center when the master controller moves; in which the movement parameters include a movement speed, an angle and a displacement; and
4), receiving the signal of each master manipulator by the control center, obtaining movement parameters of the slave manipulator by calculation, and then controlling the slave manipulator to act according to the movement parameters of the slave manipulator; in which the movement parameters of the slave manipulator include a movement speed, an angle and a displacement.

The master manipulator connected to the master controller, the two master manipulators adjacently connected to the master manipulator which is connected to the master controller are perpendicular to each other.

Besides, a centerline of the master controller and centerlines of the two master manipulator modules adjacently connected to the master controller meet at one point. Alternatively, a centerline of the master manipulator module connected to the master controller and the centerlines of the two master manipulator modules adjacent to the master manipulator which is connected to the master controller meet at one point First Embodiment A master manipulator of a minimally invasive surgical robot includes a first master manipulator module 100, a second first master manipulator module 200 and a third master manipulator module 300 which are perpendicular to each other; an output end of the third master manipulator module 300 is connected to an input end of the second master manipulator module 200; an output end of the second master manipulator module 200 is connected to an input end of the first master manipulator module 100; and the first master manipulator module 100 is connected to a master controller 1010.

The first master manipulator module 100 and the second master manipulator module 200 are connected by a first master arm 400; the second master manipulator module 500 is provided with a second master arm 500; the third master manipulator module 300 is provided with a third master arm 600 which is transverse; and one end, away from the third master manipulator module 300, of the third master arm 600 is connected to one end, away from the second master manipulator module 200, of the second master arm 500.

A centerline of the first master manipulator module 100 and a centerline of the second master manipulator module 200 are located on a same plane.

A rotatable driving member 601 is provided at the end, away from the third master manipulator module 300, of the third master arm 600; a second connecting rod 501 is provided at the end, away from the second master manipulator module 200, of the second master arm 500; and the second connecting rod 501 is connected to a driving member 601 in a power transmitted manner.

The driving member 601 is connected to the third master manipulator module 300 through a belt transmission mechanism 605 in a power transmitted manner.

A center of the first master manipulator module 100, a center of the second master manipulator module 200 and a center of the driving member 60 meet at a same point O.

The third master arm 600 includes a third connecting rod 602 which is transverse; a third joint module 603 is provided at one end of the third connecting rod 602; a third fixing seat 604 which is fixedly connected to a fourth master manipulator module of the master manipulator is provided on a housing of the third joint module 603; and the driving member 601 is arranged at the other end of the third connecting rod 602.

The second master arm 500 is L-shaped; the second master arm 500 includes a second fixing seat 502; a second joint module 503 is provided on the second fixing seat 502; one end of the second fixing seat 502 is fixedly connected to a second cover plate A504 and the second connecting rod 501 sequentially; the other end of the second fixing seat 502 is fixedly connected to a second cover plate B505; and the second cover plate B505 is fixedly connected to the second connecting rod 501.

The first master arm 400 is L-shaped; one end of the first master arm 400 is fixedly connected to the first master manipulator module 100, and the other end of the first master arm 400 is fixedly connected to the output end of the second master manipulator module 200.

The first master manipulator module 100 includes a first fixing seat 101; a first joint module 102 is provided on the first fixing seat 101; one end of the first fixing seat 101 is fixedly connected to a first cover plate A103, a first cover plate B104 and a first connecting rod 105 sequentially; the other end of the first fixing seat 101 is fixedly connected to a first cover plate C106 and a first cover plate D107 sequentially; and the first cover plate D107 is fixedly connected to the first connecting rod 105.

The master manipulator of the minimally invasive surgical robot further includes a fourth master manipulator module 700, a fifth master manipulator 800 and a sixth master manipulator 900 which are arranged vertically from bottom to top; and the fourth master manipulator module 700 is fixedly connected to the third master manipulator module 300.

The fourth master manipulator module 700, the fifth master manipulator 800 and the sixth master manipulator 900 all include a joint module 1000;
the joint module 1000 includes a base 8; a housing 4 is fixedly connected to the base 8; a motor 3 is provided on the housing 4 through a rolling bearing 15 and a rolling bearing 16; an output shaft 5 of the motor is connected to a reducer 7 through a connecting flange 6; the reducer 7 is arranged on the base 8 through a cross rolling bearing 13; and the reducer 7 transmits power to an output flange 12.

A position encoder 11 is provided on an outer circular surface of the output flange 12, to control an angle rotated by the motor, so as to control an actual position of the first connecting rod, the second connecting rod and the third connecting rod.

An output end of the reducer 7 is fixed to a connecting flange 9; the output flange 12 is fixedly connected to the connecting flange 9; and a torque sensor 10 is provided between the connecting flange 9 and the output flange 12. A torque of the output flange 12 is measured by the torque sensor 10 when the motor 3 is powered off, so as to control the motor 3 to rotate reversely properly, which realizes the force balance of the output flange.

One end, away from the output flange 12, of the base 8 is fixed to a cable sleeve fixing seat 17; a cable sleeve 1 is fixed in the cable sleeve fixing seat 17; the cable sleeve 1 is passed through the motor 3 and the reducer 7 sequentially; and the cable sleeve 1 is supported on the connecting flange 6 through a rolling bearing 14.

A speed encoder 2 is provided at one end, away from the output flange 12, of the cable sleeve 1, so as to control the rotation speed of the motor.

A structure of the first master manipulator module 100 and a structure of the third master manipulator module 300 and a structure of the second master manipulator module 200 are same, which all include a housing and a joint module 1000' which is arranged in the housing;
the joint module 1000' includes a base 1' which is fixedly connected to the housing; a motor 2' is provided on the base 1' through a first bearing 7'; an output shaft 3' of the motor is connected to a reducer 4'; the reducer 4' is arranged on the base 1' through a bearing 6'; the reducer 4' transmits power to an output flange 5';
one end of the first master arm 400' is fixed to the housing of the first master manipulator module 100, the other end of the first master arm 400' is fixed to an output flange of the second master manipulator module 200;
one end of the second master arm 500' is fixed to the housing of the second master manipulator module 200, the other end of the second master arm 500' is fixed to an output flange of the third master manipulator module 300; and
one end of the third master arm 600' is fixed to the output flange of the third master manipulator module 300.

A position encoder 15' is provided on an outer circular surface of the output flange 5'.

An output end of the reducer 4' is fixed to an intermediate member 8'; and the output flange 5' is fixedly connected to the intermediate member 8'.

A torque sensor 16' is provided between the intermediate member 8' and the output flange 5'.

A cable sleeve fixing seat 13' is provided at one end, away from the output flange 5', of the base 1'; a cable sleeve 14' is fixed in the cable sleeve fixing seat 13; the cable sleeve 14' is passed through the motor 2' and the reducer 4' sequentially; and the cable sleeve 14' is supported by spaced bearings 18'.

A speed encoder 17' is provided at one end, away from the output flange 5', of the cable sleeve 14'.

The output flange of the second master manipulator module 200 is fixed to a first disc-shaped member 9' by a bolt; the first disc-shaped member 9' is fixed to a second disc-shaped member 10' by a bolt; and an edge of the second disc-shaped member 10' is fixed to a rear end of the first master arm 400 by a bolt; and
the output flange of the third master manipulator module 300 is fixed to a third disc-shaped member 11' by a bolt; the third disc-shaped member 11' is fixed to a fourth disc-shaped member 12' by a bolt; and an edge of the fourth disc-shaped member 12' is fixed to a rear end of the second master arm 500' by a bolt.

In the structure of the master manipulator of the minimally invasive surgical robot according to the present application, the fourth master manipulator module 700 is fixedly connected to the third master manipulator module 300, the third joint module 603 of the third master manipulator module 300 drives the driving member 601 to rotate, and further drives the second master manipulator module 200 to rotate. The second joint module of the second master manipulator module 200 drives the first master arm 400 to move, and further drives the first master manipulator module 100 to move. In this case, the angle rotated by the motor is controlled by the position encoder 11 provided on the outer circular surface of the output flange 12, so as to control the actual position of the first connecting rod, the second connecting rod and the third connecting rod. In addition, the master manipulator modules are located above the third master arm which is transverse, which reduces the size of the master manipulator in the vertical direction and effectively avoids the interference between the master manipulator and other components in the vertical direction.

It should be noted that the joint module 1000' and the joint module 1000 can be used alternately, that is, the joint module 1000' may be arranged on the fourth master manipulator module 700, the third master manipulator module 800 and the sixth master manipulator module, and the joint module 1000 may be arranged on the first master manipulator module 100, the second master manipulator module 200 and the third master manipulator module 300.

Second Embodiment

Figure 9:
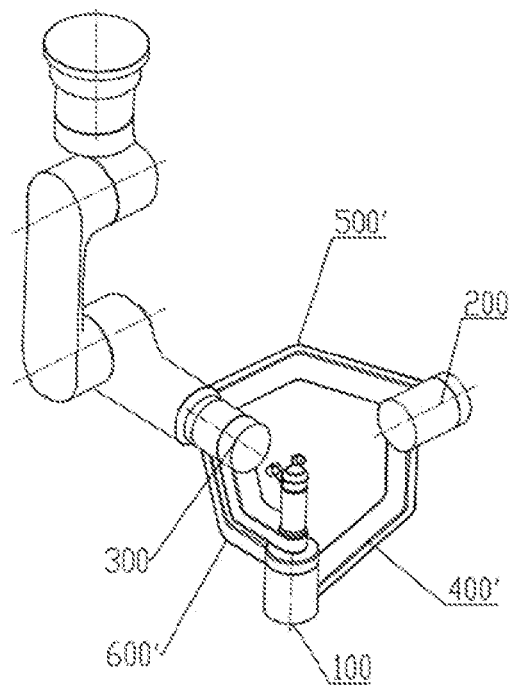
FIG. 9 is a schematic structural view of a master manipulator of a minimally invasive surgical robot according to a second embodiment of the present application.
Figure 10:
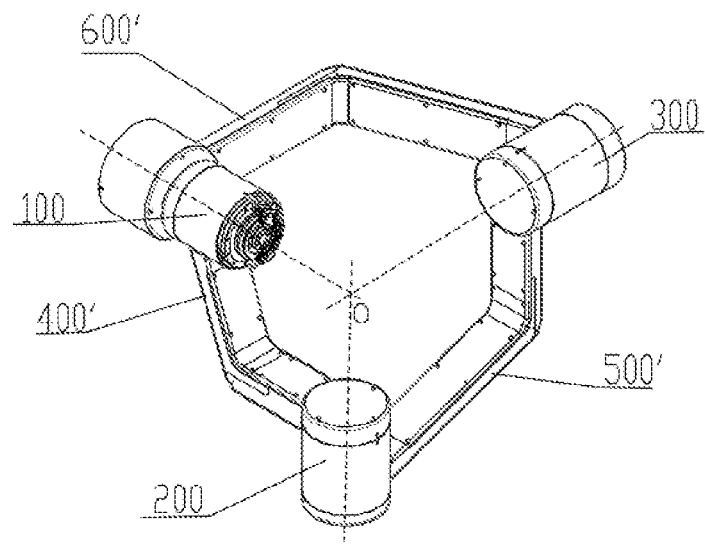
FIG. 10 is a schematic structural view of the master manipulator of the minimally invasive surgical robot according to a second embodiment of the present application.
Figure 11:
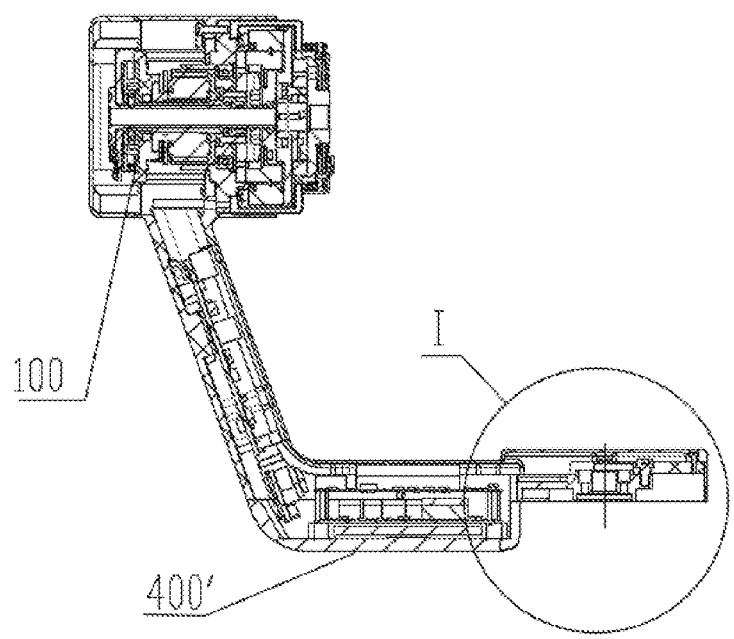
FIG. 11 is a schematic structural view of a first master manipulator module of the master manipulator of the minimally invasive surgical robot according to the second embodiment of the present application.
Figure 12:
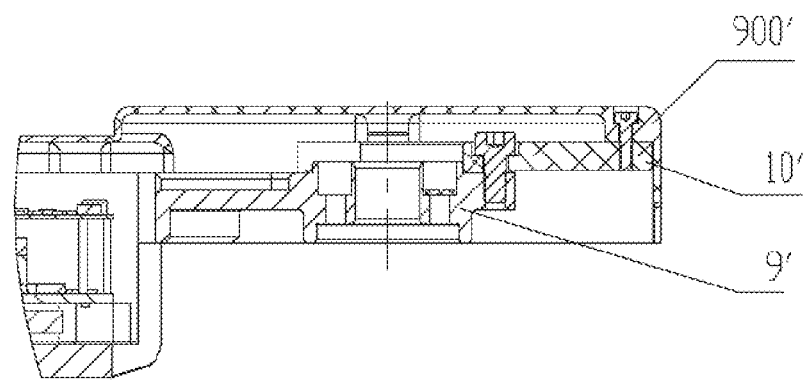
FIG. 12 is a schematic partial enlarged structural view at I portion in FIG. 9.

Referring to FIGS. 9 to 12, a master manipulator of a minimally invasive surgical robot is provided. In this embodiment, the first master manipulator module 100 and the second master manipulator module 200 are connected by a first master arm 400'; the third master manipulator module 300 and the second master manipulator module 200 are connected by a second master arm 500; and the third master manipulator module 300 is fixed to a fourth master manipulator module of the minimally invasive surgical robot by a third master arm 600'.

A centerline of the first master manipulator module 100 and a centerline of the third master manipulator module 300 are located on a same plane; and
  a center of the first master manipulator module 100, a center of the third master manipulator module 300 and a center of the second master manipulator module 200 meet at a same point O.

In the structure of the master manipulator of the minimally invasive surgical robot according to the present application, the first master manipulator module 100 is connected to the master controller 1010, and different angles are rotated by the output flanges of the joint modules by controlling the joint modules of the master manipulator modules, so as to control spatial positions of the master controller 1010 and the subsequently connected fourth master manipulator module, the fifth master manipulator module and the sixth master manipulator module, and realize precise positioning of the surgery. In addition, the surgical precision is further improved by the sensors.

More importantly, the master controller 1010 does not generate torque to the master manipulator module if the moving direction of the master controller 1010 passes through the centerline of a certain master manipulator module when the master controller 1010 moves, so that the master manipulator module does not generate rotational movement, which greatly simplifies the amount of data processed by the control center. The control center controls the slave manipulator 900' to move after data calculation. During the operation of the slave manipulator 900', the signal can also be sent to the master controller 1010 through force feedback, so as to remind a doctor to fine-tune the surgical operation.

Furthermore, the center of the first master manipulator module 100, the center of the second master manipulator module 200 and the center of the third master manipulator module 300 meet at a same point O, so that the control center does not need to separately calculate a displacement difference of an initial origin of each master manipulator module when data of the three master manipulator modules is processed, so as to further simplify the calculation.

The preferred embodiments according to the present application are described above in detail. It should be understood that, according to the concept of the present application, many modifications and changes can be made by those skilled in the art without any creative efforts. Therefore, any technical solution that can be obtained through logic analysis, reasoning or limited experimentation on the basis of the prior art by a person skilled in the art according to the concept of the present application should be within the scope of protection determined by the appended claims.

What is claimed is:

1. A master manipulator of a minimally invasive surgical robot, comprising a first master manipulator module, a second master manipulator module and a third master manipulator module which are perpendicular to each other in three dimensions, a fourth master manipulator module, a fifth master manipulator module and a sixth master manipulator module which are connected vertically from bottom to top; wherein an output end of the third master manipulator module is connected to an input end of the second master manipulator module; an output end of the second master manipulator module is connected to an input end of the first master manipulator module; and the first master manipulator module is connectable to a master controller, and the fourth master manipulator module is fixedly connected to the third master manipulator module,
  wherein the first master manipulator module and the second master manipulator module are connected by a first master arm; the second master manipulator module is provided with a second master arm; the third master manipulator module is provided with a third master arm; and one end, away from the third master manipulator module, of the third master arm is connected to one end, away from the second master manipulator module, of the second master arm,
  the first master manipulator module, the second master manipulator module, the third master manipulator module, the fourth master manipulator module, the fifth master manipulator module and the sixth master manipulator module are all located above the third master arm,
  wherein the first master manipulator module comprises a first joint module, the second master manipulator module comprises a second joint module, and the third master manipulator module comprises a third joint module,
  wherein each of the first joint module, the second joint module and the third joint module comprises a first motor,
  wherein the fourth master manipulator module comprises a fourth joint module, the fifth master manipulator module comprises a fifth joint module and the sixth master manipulator module comprises a sixth joint module,
  wherein each of the fourth joint module, the fifth joint module, and the sixth joint module comprises a second motor.

2. The master manipulator of the minimally invasive surgical robot according to claim 1, wherein a centerline of the first master manipulator module and a centerline of the second master manipulator module are located on a same plane.

3. The master manipulator of the minimally invasive surgical robot according to claim 1, wherein a driving member, which is rotatable, is provided at the end, away from the third master manipulator module, of the third master arm; a second connecting rod is provided at the end, away from the second master manipulator module, of the second master arm; and the second connecting rod is connected to the driving member in a mechanical torque transmitted manner.

4. The master manipulator of the minimally invasive surgical robot according to claim 3, wherein the driving member is connected to the third master manipulator module through a belt transmission mechanism in a mechanical torque transmitted manner.

5. The master manipulator of the minimally invasive surgical robot according to claim 3, wherein axes running through each of the first master manipulator module, the second master manipulator module and the driving member meet at a point.

6. The master manipulator of the minimally invasive surgical robot according to claim 3, wherein the third master arm comprises a third connecting rod; the third joint module is provided at one end of the third connecting rod; a third fixing seat, which is fixedly connected to the fourth master manipulator module of the master manipulator, is provided on a housing of the third joint module; and the driving member is arranged at the other end of the third connecting rod.

7. The master manipulator of the minimally invasive surgical robot according to claim 3, wherein the second master arm is L-shaped; the second master arm comprises a second fixing seat; the second joint module is provided on the second fixing seat; one end of the second fixing seat is fixedly connected to a first cover plate and the second connecting rod sequentially; the other end of the second fixing seat is fixedly connected to a second cover plate; and the second cover plate is fixedly connected to the second connecting rod.

8. The master manipulator of the minimally invasive surgical robot according to claim 1, wherein the first master arm is L-shaped; one end of the first master arm is fixedly connected to the first master manipulator module, and the other end of the first master arm is fixedly connected to the output end of the second master manipulator module.

9. The master manipulator of the minimally invasive surgical robot according to claim 1, wherein the first master manipulator module comprises a first fixing seat; the first joint module is provided on the first fixing seat; one end of the first fixing seat is fixedly connected to a third cover plate, a fourth cover plate and a first connecting rod sequentially; the other end of the first fixing seat is fixedly connected to a fifth cover plate, a sixth cover plate sequentially; and the sixth cover plate is fixedly connected to the first connecting rod.

10. The master manipulator of the minimally invasive surgical robot according to claim 1, wherein
each of the fourth joint module, the fifth joint module and the sixth joint module comprises a base; a housing is fixedly connected to the base; the second motor is provided on the housing through a first rolling bearing and a second rolling bearing; an output shaft of the second motor is connected to a reducer through a first connecting flange; the reducer is arranged on the base through a cross rolling bearing; and the reducer transmits power to an output flange.

11. The master manipulator of the minimally invasive surgical robot according to claim 10, wherein a position encoder is provided on an outer circular surface of the output flange.

12. The master manipulator of the minimally invasive surgical robot according to claim 10, wherein an output end of the reducer is fixed to a second connecting flange; the output flange is fixedly connected to the second connecting flange; and a torque sensor is provided between the second connecting flange and the output flange.

13. The master manipulator of the minimally invasive surgical robot according to claim 10, wherein one end, away from the output flange, of the base is fixed to a cable sleeve fixing seat; a cable sleeve is fixed in the cable sleeve fixing seat; the cable sleeve is passed through the second motor and the reducer sequentially; and the cable sleeve is supported on the first connecting flange through a third rolling bearing.

14. The master manipulator of the minimally invasive surgical robot according to claim 13, wherein a speed encoder is provided at one end, away from the output flange, of the cable sleeve.

15. The master manipulator of the minimally invasive surgical robot according to claim 1, wherein
each of the first joint module, the second joint module and the third joint module comprises a base which is fixedly connected to a housing; the first motor is provided on the base through a first bearing; an output shaft of the first motor is connected to a reducer; the reducer is arranged on the base through a second bearing; the reducer transmits power to an output flange;
one end of the first master arm is fixed to the housing of the first master manipulator module, the other end of the first master arm is fixed to an output flange of the second master manipulator module;
one end of the second master arm is fixed to the housing of the second master manipulator module, the other end of the second master arm is fixed to an output flange of the third master manipulator module; and
one end of the third master arm is fixed to the output flange of the third master manipulator module.

16. The master manipulator of the minimally invasive surgical robot according to claim 15, wherein a position encoder is provided on an outer circular surface of the output flange.

17. The master manipulator of the minimally invasive surgical robot according to claim 15, wherein an output end of the reducer is fixed to an intermediate member; and the output flange is fixedly connected to the intermediate member.

18. The master manipulator of the minimally invasive surgical robot according to claim 17, wherein a torque sensor is provided between the intermediate member and the output flange.

19. The master manipulator of the minimally invasive surgical robot according to claim 15, wherein a cable sleeve fixing seat is provided at one end, away from the output flange, of the base; a cable sleeve is fixed in the cable sleeve fixing seat; the cable sleeve passes through the first motor and the reducer sequentially; and the cable sleeve is supported by spaced bearings.

20. The master manipulator of the minimally invasive surgical robot according to claim 19, wherein a speed encoder is provided at one end, away from the output flange, of the cable sleeve.

21. The master manipulator of the minimally invasive surgical robot according to claim 15, wherein the output flange of the second master manipulator module is fixed to a first disc-shaped member by a bolt; the first disc-shaped member is fixed to a second disc-shaped member by a bolt; and an edge of the second disc-shaped member is fixed to a rear end of the first master arm by a bolt; and
the output flange of the third master manipulator module is fixed to a third disc-shaped member by a bolt; the third disc-shaped member is fixed to a fourth disc-shaped member by a bolt; and an edge of the fourth disc-shaped member is fixed to a rear end of the second master arm by a bolt.

* * * * *